Figure 1:
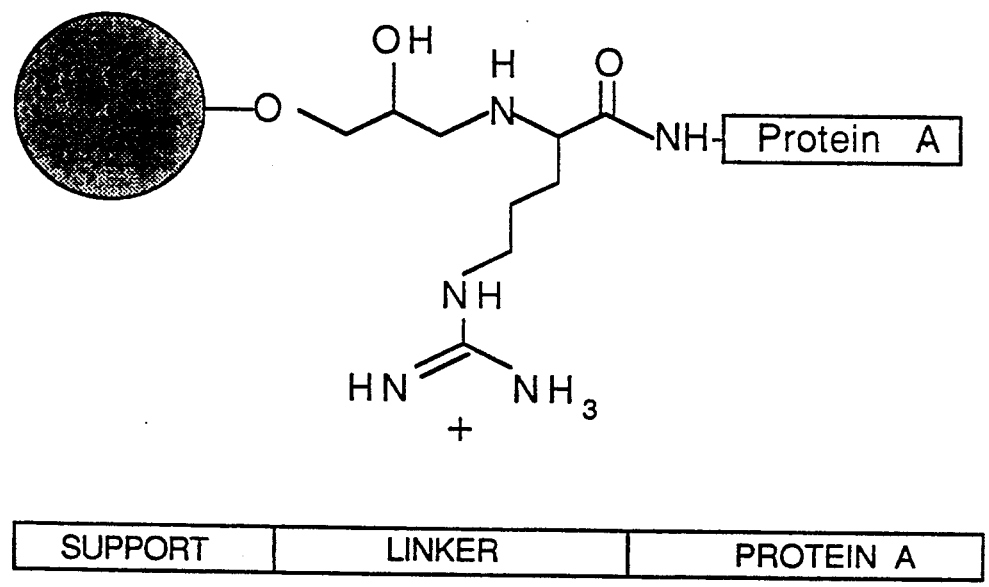

United States Patent [19]

Profy et al.

[11] Patent Number: 5,089,605
[45] Date of Patent: Feb. 18, 1992

[54] IMMOBILIZED IMMUNOGLOBULIN-BINDING PROTEINS

[75] Inventors: Albert T. Profy, Cambridge; Margaret A. Belew, Medford; Walter C. Herlihy, Beverly, all of Mass.

[73] Assignee: Repligen Corporation, Cambridge, Mass.

[21] Appl. No.: 25,466

[22] Filed: Mar. 13, 1987

[51] Int. Cl.[5] .......................... C07K 17/06; C07K 3/18
[52] U.S. Cl. .................................. 530/402; 530/413; 530/387; 530/389; 530/391; 530/816; 436/532
[58] Field of Search ............... 530/412, 413, 387, 389, 530/391, 812, 813, 814, 815, 816, 817, 402; 436/528, 529, 530, 531, 532; 435/68

[56] References Cited

U.S. PATENT DOCUMENTS

| | | | |
|---|---|---|---|
| 4,217,338 | 8/1980 | Quash | 424/1 |
| 4,374,061 | 2/1983 | Bing | 260/112 |
| 4,376,765 | 3/1983 | Trouet et al. | 424/177 |

FOREIGN PATENT DOCUMENTS 2160530 12/1985 United Kingdom.

OTHER PUBLICATIONS

Porath, J. et al., 1970, J. Chromatog. 51: 479–489.
March, S. C. et al., "Affinity Chromatography-Old Problems and New Approaches", In Dunlap, R. B., Immobilized Biochemicals and Affinity Chromatography Plenum Press, N.Y. pp. 3–14 (1974).
Colbert, D. et al., 1984, J. Biol. Response Modif. 3(3): 255–259.
Scopes, R. K., 1982, Protein Purification, Springer-Verlag, N.Y., pp. 111–124.
Sigma Chemical Company, 1987, Catalog, pp. 146, 164.
Sigma Chemical Company, 1980 Catalog, p. 110.
Young, Jr., W. W., Y. Tamura, D. M. Wolock, and J. W. Fox (1984), "Staphlococcal Protein A Binding to the Fab Fragments of Mouse Monoclonal Antibodies", J. Immuonolgy 133(6):3163–3166.
Porath, J., and N. Fornstedt (1970) "Group Fractionation of Plasma Proteins on Dipolar Ion Exchangers", J. Chromatog 51:479–489.
Love, R., A. Profy, B. Kaylos, M. Belew, W. Herlihy (1987) "Large-Scale Production of Recominant Protein A and its use in Purifying Monoclonal Antibodies", Ucla Symposia on Molecular and Cellular Biology, New Series, 68:491–500.
Kohler, G. and Milstein, C. (1975) "Continuous Cultures of Fused Cells Secreting Antibody of Predefined Specificity", Nature 256: 495–497.
Manil, L., Motte, P., Pernas, P., Troalen. F., Bohuon, C. and Bellet, D. (1986) "Evaluation of Protocols for Purification of Mouse Monoclonal Antibodies", Journal of Immunological Methods 90: 25–37.
Seppala, J. Sravas, H. Peterfy, F. and Makela, O. (1981) "The Four Subclasses of IgG Can Be Isolated from Mouse Serum by Using Protein A–Sepharose", Scand. J. Immunol. 14:335–342.
Mackenzie, M. R., Warner, Noel L. and Mitchell, G. F. (1978) "The Binding of Murine Immunoglobulins to Staphylococcal Protein A", The Journal of Immunology 120:1493–1496.
Stephenson, J. R., Lee, J. M. and Wilton-Smith, P. D. (1984) "Production and Purification of Murine Monoclonal Antibodies: Aberrent Elution from Protein A–Sepharose 4B", Analytical Biochemistry 142:189–195.
Ey, P. L., Prowse, S. R. and Jenkin, C. R. (1978) "Isolation of Pure IgG$_1$ IgG$_{2a}$ and IgG$_{2b}$ Immunoblobulins from Mouse Serum Using Protein A–Sepharose", Immunochemistry 15:429–436.

*Primary Examiner*—Margaret Moskowitz
*Assistant Examiner*—Keith C. Furman
*Attorney, Agent, or Firm*—Saliwanchik & Saliwanchik

[57] ABSTRACT

The invention concerns unique immobilized immunoglobulin-binding protein materials which have a high binding capacity for immunoglobulins. Exemplified are preparations which have a high binding capacity for IgG1 immunoglobulins. The preparations are made by covalently joining an immobilization support material to (a) an arginine-containing linker and (b) an immunoglobulin-binding protein material. The immunoglobulin-binding protein can be joined to the linker through an amide bond. Specifically disclosed is an immobilized protein A preparation. This immobilized protein A preparation has utility in the art of purifying monoclonal antibodies.

31 Claims, 1 Drawing Sheet

IMMOBILIZED IMMUNOGLOBULIN-BINDING PROTEINS

Background of the Invention

Monoclonal antibodies (MAbs) produced from hybridoma cell lines were first described by Kohler and Milstein (Kohler, G. and Milstein, C. [1975] Nature (London) 256:495-497). Due to their high specificity for a single antigen, MAbs have been widely used as research tools, as components of medical diagnostic tests, and as the basis for immunoaffinity purification procedures. They also show promise as agents for in vivo human therapeutic or diagnostic use.

At the current state of the art, most hybridomas are derived from mouse B lymphocytes, and, consequently, the resulting MAbs are murine immunoglobulins. These immunoglobulins are typically of the IgG class, with subclass IgG1 being the most common. The hybridomas are grown in the peritoneal cavity of mice or in mass culture, and the MAbs are isolated from the resulting ascites fluid or tissue culture fluid, respectively.

For most applications, and especially for human in vivo use, MAbs must be purified. This can be accomplished by a number of well-known methods, including ion exchange chromatography, adsorption chromatography, and affinity chromatography. Of these methods, affinity chromatography on a matrix consiting of Staphylococcal protein A immobilized to agarose beads, and sold, for example, as Protein A-Sepharose ® (Pharmacia AB, Uppsala, Sweden), has been found to give the most highly purified MAb (Manil, L., Motte, P., Pernas, P., Troalen, F., Bohuon, C. and Bellet, D. [1986] Journal of Immunological Methods 90:25-37). This procedure exploits the fact that murine IgG binds to Protein A-Sepharose ® at pH>8.0, but does not bind at pH<3.0. Typically, the pH of the MAb-containing solution is adjusted to 8.5 and passed over a column of Protein A-Sepharose ®. With the MAb bound to the protein A, contaminants are washed from the column with a pH 8.5 buffer. Finally, the purified MAb is eluted by passing a pH 3.0 buffer over the column. The purity of the eluted antibody generally exceeds 90%.

The usefulness of Protein A-Sepharose ® for the purification of murine-derived MAbs of subclass IgG1, however, is extremely limited. This is due to the exceptionally low affinity of the IgG1 subclass for this material, which results in a low binding capacity (defined as mg IgG/ml gel) for MAbs of subclass IgG1. Seppala et al. (Seppala, I., Sarvas, H., Peterfy, F. and Makela, O. [1981] Scand. J. Immunol. 14:335-342) reported that IgG1 from mouse serum eluted from Protein A-Sepharose ® at pH 6.0-7.0, higher than the pH 3.5-5.0 at which the other IgG subclasses elute. Similarly, MacKenzie et al. (MacKenzie, M. R., Warner, N. L. and Mitchell, G. F. [1978] J. Immunol. 120:1493-1496) found that murine IgG1, again from polyclonal serum, eluted from Protein A-Sepharose ® columns at a lower concentration of sodium thiocyanate (0.5M) than was required to elute the other subclasses (1.5-2.0M). Consistent with the properties of polyclonal serum, Protein A-Sepharose ® has a lower binding capacity for MAbs of murine subclass IgG1 than for MAbs of the other IgG subclasses, although the affinities of individual IgG1 MAbs tend to vary somewhat (Manil et al. supra, Stephensen, J. R., Lee, J. M. and Wilton-Smith, P. D. [1984] Anal. Biochem. 142:189-195). In many cases, standard affinity chromatography procedures give a very low recovery of IgG1 MAbs, and purification by more difficult and less effective methods is sometimes required.

Other commercially available matrices consisting of protein A immobilized to agarose, such as Affi-Gel ® Protein A (Bio-Rad Laboratories, Richmond, Calif.) and protein A-agarose (Pierce Chemical Company, Rockford, Ill.) appear to exhibit, like Protein A-Sepharose ®, low binding capacity for murine MAbs of subclass IgG1 when the purification conditions of Ey et al. (Ey, P. L., Prowse, S. J. and Jenkin, C. R. [1978] Immunochemistry 15:429-436) are used. These limitations have been recognized by commercial suppliers who have attempted to overcome them by the use of proprietary binding solutions such as the MAPS ® II system (Bio-Rad Laboratories) and the MonoPure ™ system (Pierce Chemical Company, Rockford, Ill.). However, these solutions are expensive, and their components may not be compatible with MAbs intended for human in vivo use. Also, some samples, such as tissue culture fluid, cannot be chromatographed directly, but require instead involved preparation before addition to the column.

Brief Summary of the Invention

The subject invention concerns improved immobilized immunoglobulin-binding proteins, and processes for preparing and using the same. Exemplified is an improved immobilized protein A preparation which has high binding capacity for human and mouse immunoglobulin of subclass IgG1. More particularly, the exemplified material concerns immobilized protein A preparations comprising an immobilization support material which is covalently joined to (a) an arginine-containing linker, and (b) protein A or a protein A-like material. The protein A or protein A-like material can be joined to the linker through an amide bond. Specifically exemplified herein is Immobilized rPROTEIN A (Trademark of Repligen Corporation, Cambridge, Mass.), which is characterized as crosslinked 4% agarose joined covalently through an N-(2-hydroxypropyl)arginine linker, via an amide bond, to rPROTEIN A (Trademark of Repligen Corporation, Cambridge, Mass.) having the amino acid sequence shown in Chart A.

FIG. 1 depicts the invention as exemplified by protein A. However, as discussed above, the invention includes other immunoglobulin-binding proteins.

The immobilization support material can be any support used in immunoassays, for example, filter paper, plastic beads or test tubes made from polyethylene, polystyrene, polypropylene or other suitable material. Especially useful are particulate materials such as agarose, crosslinked dextran, and other polysaccharides. The techniques for such bonding are well known to those skilled in the art. In a general sense, the art related to covalent attachment of enzymes to solid supports is relevant as a source of immobilization support materials. A variety of supports have been used in the enzyme art, including porous glass and ceramics, stainless steel, sand, charcoal, cellulose, synthetic polymers, and metallic oxides. An essential criterion for the support is that it is non-toxic to the biological materials, i.e., it does not reduce the biological activity of the materials it is contacted with.

Protein A can be derived from natural Staphylococcal sources by procedures well known in the art. Protein A and protein A-like materials can be obtained via recombinant DNA procedures; one such procedure is disclosed herein for exemplary purposes.

The linker can consist of arginine coupled to the support directly, or through a chemical chain of any length or composition normally used in immobilizations. The chemical chain can be another protein. Arginine can be coupled to cyanogen bromide-treated support, sodium periodate-treated support, carbonyldiimidazole-treated support, divinylsulfone-treated support, N-ethoxycarbonyl-2-ethoxy-1,2-dihydroquinoline-(EEDQ)-treated support, trichloro-s-triazine-treated support, benzoquinone-treated support, and the like. In addition, the linker can consist of any N-alkyl-, N-aryl-, N-acyl-, N-oxycarbonyl-, or N-imidoarginine moiety. The preferred linker is N-(2-hydroxypropyl)arginine.

The immobilized protein A preparations of the invention overcome some of the limitations of commercial preparations for purifying immunoglobulins, especially IgG1.

Descripton of the Drawing

FIG. 1: A schematic of immobilized protein A.

Ddetailed Description of the Invention

The immobilized rPROTEIN A of the invention can be prepared by the following procedures, which are not to be construed as limiting, but merely as exemplary:

(1) Preparation of arginine-agarose

The procedure was similar to that described by Porath and Fornstedt (Porath, J. and Fornstedt, N. [1970] J. Chromatogr. 51:479–489). Crosslinked 4% agarose gel was washed several times with distilled water and the excess liquid was removed. The gel was resuspended in an equal volume of 1.0M NaOH. Onetenth volume of epichlorohydrin was added, and the mixture gently mixed at room temperature to 37° C. overnight. The gel was washed extensively with water until the pH dropped into the neutral range. Arginine was coupled to this epichlorohydrin-activated gel by removing the excess water from the gel and resuspending it in an equal volume of 0.01M NaOH to which 0.1 g of arginine per ml of gel had been added. This suspension was mixed overnight at room temperature to 37° C. After coupling, the gel was washed to neutral pH with water.

(2) Activation of arginine-agarose

The arginine-agarose gel from (1) was gradually dried by washing it first with 5 volumes of 50% solvent (isopropyl alcohol or dioxane) in water. This was increased to 100% solvent in 4 rapid washes. At no point was the gel allowed to dry. The gel was then suspended in a 3- to 5-fold volume excess of solvent and agitated at room temperature overnight. This was followed by 3 30-min solvent washes, each also with a 3- to 5-fold volume excess. Next, the gel was suspended in an equal volume of solvent. N-Hydroxysuccinimide (NHS) was added to a level of 24–120 mg/ml of gel, and the mixture shaken until the NHS dissolved. Dicyclohexylcarbodiimide (DCC) was then added to a level of 40–200 mg/ml of gel, and the entire mixture shaken at room temperature for 2 hr. After this time, the mixture was opaque due to the accumulation of the insoluble by-product N,N'-dicyclohexylurea. The mixture was washed 3 to 4 times with a 5- to 10-fold volume excess of solvent. This was followed sequentially by 2 5- to 10-fold volume excess washes of methyl alcohol, 2 5- to 10-fold volume excess washes of dimethyl sulfoxide, and 2 5- to 10-fold volume excess washes of methyl alcohol. Finally, the gel was washed 3 to 4 more times with a 5- to 10-fold volume excess of solvent.

(3) Coupling of protein A to Activated Arginine-Agarose

A protein A-like polypeptide was reacted with the activated arginine-agarose gel described in (2). The production of this polypeptide from the recombinant plasmid pBG3-2ΔN in the Escherichia coli K12 host PR13 is described infra. To effect the coupling, the activated gel was rehydrated by washing it quickly several times with a 5-fold volume excess of cold distilled water. The support was then washed quickly with cold 0.1M 4-(2-hydroxyethyl)-1-piperazine ethanesulfonic acid (HEPES) buffer, pH 5.0. The excess buffer was removed and a solution of 5 mg protein A-like material per ml of gel in a 2-fold volume excess of 0.1M HEPES, pH 5.0 was added. The reaction mixture was shaken overnight at 4° C. for 4 hr at room temperature. At the end of this time, the coupling supernatant was collected and the gel was washed with a 5-fold volume excess of 0.1M HEPES, pH 5.0 containing 1.0M sodium chloride. The wash was combined with the coupling supernatant and assayed for protein concentration by conventional procedures (e.g., biuret), well known to those familiar with the art. After washing, the gel was shaken with a 2-fold volume excess of 1M ethanolamine, pH 8.0 for 2 hr at room temperature. After this time, the gel was washed with a 5- to 10-fold volume excess of water.

(4) Preparation of Protein A via Recombinant Host Microbe

Recombinant host E. coli NRRL B-15909 was grown under suitable conditions to prepare protein A. Fermentation was performed in a 201 Chemapec fermentor (Chemapec, Inc. Woodbury, N.Y.) fitted with dO₂ and pH control. Recombinant cells were grown at a dO₂ of 50% (air = 100%) at the pH indicated. pH was adjusted by addition of 5M NH$_4$OH or 5M H$_2$SO$_4$, or by the use of metabolizable organic acids as required. Foam was controlled by addition of antifoam B (E.I. Du Pont de Nemours & Co., Inc., Wilmington, Del.). Fermentation temperature was 37° C.; all fermentations were conducted with a final volume of 9.5 liters.

The culture disclosed in this application has been deposited in the Agricultural Research Service Patent Culture Collection (NRRL), Northern Regional Research Center, 1815 North University Street, Peoria, Ill. 61604, U.S.A.

| Culture | Repository No. | Deposit date |
|---|---|---|
| Escherichia coli | NRRL B-15909 | November 20, 1984 |

The subject culture has been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

A 0.5 kg wet well weight (wcw) cell pellet of *E. coli* NRRL B-15909, containing a plasmid coding for the production of protein A, is resuspended in homogenization buffer (8.75 mM Tris-(hydroxymethyl)aminomethane. HCl pH 8.3, 2 mM potassium ethylenediaminetetraacetic acid [KEDTA], 0.1 mM phenylmethylsulfonylfluoride [PMSF], 0.5% Triton ® X-100 [Rohm & Haas Co., Philadelphia, Pa.]). The cell suspension is passed through a Dyno-Mill ® KDL-pilot model (Dyno-Mill ® (an instrument that employs glass beads to mechanically disrupt cells) [a bead mill] supplied by Impandex. Maywood, N.J.). The Dyno-Mill ® is charged with 1.2 liters of dry glass beads (0.5-0.7 mm diameter) and operated at the highest speed setting. The cell suspension is fed to the Dyno-Mill ® at a rate of 200 ml/min. After the cell suspension has passed through the bead mill, the mill is washed with an additional 2 liters of homogenization buffer.

The lysate is centrifuged at 4,000 rpm for 120 min in a Beckman SA-62 centrifuge (Beckman Instruments, Inc., Fullerton, Calif.). After centrifugation, the pellet is discarded and the supernatant is clarified by passage through a 0.20-μm Microgon (a conventional 0.2 micron hollow fiber filter) filter (Microgon, Laguna Hills, Calif.). The retained volume is taken to 40% of the starting volume and washed with 3 volumes of additional homogenization buffer. The pH of the filtrate is adjusted to 8.3 and 1N NaOH, and the conductivity adjusted to 2.0 mS/cm by diluting with distilled $H_2O$.

The pH 8.3 filtrate, obtained above, is loaded onto a 14×95 cm column packed with Whatman DE-52 cellulose (Whatman Laboratory Products, Inc., Clifton N.J.) which has been previously equilibrated in column 1 equilibration buffer (35 mM Tris.HCl pH 8.3, 2 mM KEDTA, 0.1 mM PMSF) at a flow rate of 6.0 liter/hr. (This flow rate is maintained throughout all ion exchange column 1 operations.) The column is then washed with 10-15 liters of column 1 equilibration buffer and then eluted with a linear gradient containing 35 liters of column 2 equilibration buffer (35 mM Tris.HCl, pH 8.1) and 35 liters of column 1 gradient buffer (35 mM Tris.HCl pH 8.3, 200 mM KCl, 2 mM KEDTA, 0.1 mM PMSF). Fractions are collected and assayed for protein A using size exclusion HPLC. It is found that most of the contaminating proteins are not retained by the DEAE cellulose and are removed by washing the column with equilibration buffer. Protein A of 80-90% purity is eluted from the column at 80 mM KCl.

The protein A-containing fractions from column 1 are pooled and adjusted to pH 8.1 by addition of 6M HCl. The conductivity of this solution is adjusted to 2.0 mS/cm by dilution with distilled water. This material is loaded onto a 5×180 cm column packed with Pharmacia DEAE Fast Flow (a highly cross-linked agarose bead capable of withstanding high flow rates. DEAE-Sepharose Fast Flow contains DEAE [diethylaminoethyl] groups that provide a positive charge to facilitate anion exchange chromatography.) Sepharose in column 2 equilibration buffer. A 0.2-μm filter is connected to the inlet port of this column to prevent bacterial contamination. A flow rate of 2.0 liters/hr is used for this column. After loading, 6 liters of column 2 equilibration buffer is used to wash the column followed by elution with a linear gradient containing 10 liters of column 2 equilibration buffer and 10 liters of column 2 gradient buffer (35 mM Tris.HCl pH 8.1, 200 mM KCl). Under these conditions contaminating proteins do not bind to the column. Protein A elutes from the column as a well-resolved gaussian peak at 70 mM KCl. This material is found to be greater than 99% pure by SDS gel electrophoresis and size exclusion HPLC. Similarly with column 1, a wide variety of anion exchange columns can be used in this step, so long as protein A will bind to the column under initial conditions, then be eluted in a pure form by an ionic strength gradient.

rPROTEIN A has the amino acid sequence shown in Chart A.

As disclosed above, other preparations of protein A can be used in the subject invention. These preparations can be prepared by recombinant procedures using vectors constructed with different regulatory regions, e.g., promoters, than the vector disclosed herein. Also, the invention encompasses the use of individual protein A domains, e.g., domains E, A, B, C, and D, which can be used to provide immobilized protein A-like materials having high affinity for human or mouse immunoglobulin subclass IgG1. Still further, non-recombinant protein A preparations can be used to join to a linker as disclosed herein to provide immobilized protein A preparations having high affinity for IgG1.

The high binding capacity of Immobilized rPROTEIN A for mouse immunoglobulin of subclass IgG1 is demonstrated in the following examples.

Example 1

The affinities of Immobilized rPROTEIN A and Protein A-Sepharose ® for human polyclonal IgG, mouse polyclonal IgG, and three MAbs of mouse subclass IgG1 were measured. Human polyclonal IgG and mouse polyclonal IgG were purchased from the Sigma Chemical Company, St. Louis, Mo., and dissolved to a concentration of 10 mg/ml with 0.1M potassium phosphate, pH 8.5. The anti-β-lactamase MAbs 103-13, 103-23, and 103-28 were the generous gift of Dr. Jennifer Jackson, Repligen Corporation. The subclass of each was determined to be IgG1, using the Mouse Immunoglobulin Subtype Identification Kit, available from Boehringer Mannheim Biochemicals, Indianapolis, Ind. Ammonium sulfate fractions containing each MAb were diluted with 2 volumes of 0.1M potassium phosphate, pH 8.5, giving a final MAb concentration of approximately 10 mg/ml.

Binding capacities (mg IgG bound/ml gel) were measured as follows: 50 μl of affinity gel was washed with 2 400-μl portions of 0.1M potassium phosphate, pH 8.5. The gel was then treated with 200 μl of antibody solution and agitated for 30 min at room temperature. The supernatant was then removed and the settled gel washed with 2 400-μl portions of 0.1M potassium phosphate, pH 8.5. These washes were pooled with the supernatant and the concentration of antibody determined by the absorbance of the solution at 280 nm (a 1 mg/ml solution of human IgG gives an absorbance of 1.3 and a 1 mg/ml solution of mouse IgG gives an absorbance of 1.4). The difference between the amount of antibody added to the gel and the amount remaining in the pooled supernatant and washes was used to calculate the binding capacity. To obtain a more direct measurement, the washed gel was agitated with 2 300-μl portions of 0.2M glycine hydrochloride (pH 2.0), and the absorbance at 280 nm of the pooled glycine washes was measured and used to determine the binding capacity.

The binding capacities of Immobilized rPROTEIN A and Protein A-Sepharose ® for the different antibodies are shown in Table 1. The values were obtained by averaging the difference and direct measurements described above. The binding capacity of Immobilized rPROTEIN A for human IgG is 35% higher than that of Protein A-Sepharose ®. The binding capacity for mouse polyclonal IgG is 55% higher, and the binding capacities for the IgG1 MAbs are 250 to 700% higher.

TABLE 1

| | Binding Capacity (mg IgG/ml Gel) | |
|---|---|---|
| Antibody | Protein A-Sepharose ® | Immobilized rPROTEIN A |
| Human IgG | 17 | 23 |
| Mouse IgG | 11 | 17 |
| MAb 103-13 | 2 | 7 |
| MAb 103-23 | 1 | 6 |
| MAb 103-28 | 1 | 8 |

The above shows that Immobilized rPROTEIN A offers an advantage over Protein A-Sepharose ® for the purification of both human and mouse IgG. The advantage is particularly clear for murine MAbs of Subclass IgG1.

EXAMPLE 2

The effect of buffers optimized for binding murine IgG1 on the binding capacities of the Immobilized rPROTEIN A and Protein A-Sepharose ® gels was determined. The experiment described in Example 1 was repeated with the substitution of an optimized buffer formulation (1.5M glycine, pH 9.0, 3M NaCl) for 0.1M potassium phosphate, pH 8.5. The capacities are shown in the following table:

TABLE 2

| | Binding Capacity (mg IgG/ml Gel) | |
|---|---|---|
| Antibody | Protein A-Sepharose ® | Immobilized rPROTEIN A |
| Human IgG | 16 | 21 |
| Mouse IgG | 13 | 17 |
| MAb 103-13 | 8 | 13 |
| MAb 103-23 | 6 | 9 |
| MAb 103-28 | 10 | 16 |

Use of the optimized buffer does not increase the binding capacity of Immobilized rPROTEIN A for human and mouse polyclonal IgG, but increases the binding capacity for the IgG1 MAbs by 50-90%. By contrast, the binding capacity of Protein A-Sepharose ® for mouse polyclonal IgG is increased 18% and the capacities for the IgG1 MAbs are increased 300-900%. Thus, the structure of Immobilized rPROTEIN A permits 50-66% of the optimal binding capacity for mouse IgG1 to be achieved with 0.1M potassium phosphate, pH 8.5, whereas Protein A-Sepharose ® achieves only 10-25% of the optimal capacity under these conditions.

As can be seen by comparing Examples 1 and 2, Immobilized rPROTEIN A exhibits an IgG1 binding capacity in the absence of the optimized buffer that is equivalent to the capacity of Protein A-Sepharose ® in the presence of optimized buffer. Furthermore, the binding capacities of Immobilized rPROTEIN A in optimized buffer are higher than those of other commercially available products.

The above examples show that the immobilized protein A preparations of the invention are useful to purify preparations of IgG1. Also, they can be used in immunoassays using standard procedures well known in the art.

The invention procedure can be used to immobilize other immunoglobulin-binding proteins, such as Streptococcal protein G and rabbit anti-mouse IgG immunoglobulins.

Chart A
Amino Acid Sequence of rProtein A ™

Met Leu Arg Pro Val Glu Thr Pro Thr Arg Glu Ile Lys Lys
Leu Asp Gly Leu Ala Gln His Asp Glu Ala Gln Gln Asn Ala
Phe Tyr Gln Val Leu Asn Met Pro Asn Leu Asn Ala Asp Gln
Arg Asn Gly Phe Ile Gln Ser Leu Lys Asp Asp Pro Ser Gln
Ser Ala Asn Val Leu Gly Glu Ala Gln Lys Leu Asn Asp Ser
Gln Ala Pro Lys Ala Asp Ala Gln Gln Asn Lys Phe Asn Lys
Asp Gln Gln Ser Ala Phe Tyr Glu Ile Leu Asn Met Pro Asn
Leu Asn Glu Glu Gln Arg Asn Gly Phe Ile Gln Ser Leu Lys
Asp Asp Pro Ser Gln Ser Thr Asn Val Leu Gly Glu Ala Lys
Lys Leu Asn Glu Ser Gln Ala Pro Lys Ala Asp Asn Asn Phe
Asn Lys Glu Gln Gln Asn Ala Phe Tyr Glu Ile Leu Asn Met
Pro Asn Leu Asn Glu Glu Gln Arg Asn Gly Phe Ile Gln Ser
Leu Lys Asp Asp Pro Ser Gln Ser Ala Asn Leu Leu Ala Glu
Ala Lys Lys Leu Asn Glu Ser Gln Ala Pro Lys Ala Asp Asn
Lys Phe Asn Lys Glu Gln Gln Asn Ala Phe Tyr Glu Ile Leu
His Leu Pro Asn Leu Asn Glu Glu Gln Arg Asn Gly Phe Ile
Gln Ser Leu Lys Asp Asp Pro Ser Gln Ser Ala Asn Leu Leu
Ala Glu Ala Lys Lys Leu Asn Asp Ala Gln Ala Pro Lys Ala
Asp Asn Lys Phe Asn Lys Glu Gln Gln Asn Ala Phe Tyr Glu
Ile Leu His Leu Pro Asn Leu Thr Glu Glu Gln Arg Asn Gly
Phe Ile Gln Ser Leu Lys Asp Asp Pro Ser Val Ser Lys Glu
Ile Leu Ala Glu Ala Lys Lys Leu Asn Asp Ala Gln Ala Pro
Lys Glu Glu Asp Asn Asn Lys Pro Gly Lys Glu Asp Gly Asn
Lys Pro Gly Lys Glu Asp Gly Asn Lys Pro Gly Lys Glu Asp
Asn Lys Asn Leu Gly Lys Glu Asp Gly Asn Lys Pro Gly Lys
Glu Asp Asn Lys Lys Pro Gly Lys Glu Asp Gly Asn Lys Pro
Gly Lys Glu Asp Gly Asn Lys Pro Gly Lys Glu Asp Gly Asn
Lys Pro Gly Lys Glu Asp Gly Asn Lys Pro Gly Lys Glu Asp
Gly Asn Lys Pro Gly Lys Glu Asp Gly Asn Gly Val Ile Asp
Asp Lys Leu Ser Asn Met Arg Ile Leu Glu Asp Glu Arg Ala
Ser

We claim:

1. In a process for preparing immobilized immunoglobulin-binding protein material, wherein an immobilized support material is covalently joined, through the use of a linker, to an immunoglobulin-binding protein, and wherein aid immunoglobulin-binding protein is selected from the group consisting of protein A, any of domains A, B, C, D, and E of protein A, and any combination of domains A, B, C, D, and E or protein A; and improvement whereby said linker comprises arginine, and said immunoglobulin-binding protein is directly covalently joined to a terminal arginine of said linker.

2. The process, according to claim 1, wherein said immunoglobulin-binding protein is joined to the linker through an amide bond.

3. The process, according to claim 1, wherein said immobilization support material is crosslinked 4% agarose.

4. The process, according to claim 1, wherein said linker is N-(2-hydroxypropyl)arginine.

5. The process, according to claim 1, wherein said immunoglobulin-binding protein is produced by recombinant means.

6. The process, according to claim 5, wherein said immunoglobulin-binding protein is recombinant protein A having the following amino acid sequence:

| Met | Leu | Arg | Pro | Val | Glu | Thr | Pro | Thr | Arg | Glu | Ile | Lys | Lys |
|-----|-----|-----|-----|-----|-----|-----|-----|-----|-----|-----|-----|-----|-----|
| Leu | Asp | Gly | Leu | Ala | Gln | His | Asp | Glu | Ala | Gln | Gln | Asn | Ala |
| Phe | Tyr | Gln | Val | Leu | Asn | Met | Pro | Asn | Leu | Asn | Ala | Asp | Gln |
| Arg | Asn | Gly | Phe | Ile | Gln | Ser | Leu | Lys | Asp | Asp | Pro | Ser | Gln |
| Ser | Ala | Asn | Val | Leu | Gly | Glu | Ala | Gln | Lys | Leu | Asn | Asp | Ser |
| Gln | Ala | Pro | Lys | Ala | Asp | Ala | Gln | Gln | Asn | Lys | Phe | Asn | Lys |
| Asp | Gln | Gln | Ser | Ala | Phe | Tyr | Glu | Ile | Leu | Asn | Met | Pro | Asn |
| Leu | Asn | Glu | Glu | Gln | Arg | Asn | Gly | Phe | Ile | Gln | Ser | Leu | Lys |
| Asp | Asp | Pro | Ser | Gln | Ser | Thr | Asn | Val | Leu | Gly | Glu | Ala | Lys |
| Lys | Leu | Asn | Glu | Ser | Gln | Ala | Pro | Lys | Ala | Asp | Asn | Asn | Phe |
| Asn | Lys | Glu | Gln | Gln | Asn | Ala | Phe | Tyr | Glu | Ile | Leu | Asn | Met |
| Pro | Asn | Leu | Asn | Glu | Glu | Gln | Arg | Asn | Gly | Phe | Ile | Gln | Ser |
| Leu | Lys | Asp | Asp | Pro | Ser | Gln | Ser | Ala | Asn | Leu | Leu | Ala | Glu |
| Ala | Lys | Lys | Leu | Asn | Glu | Ser | Gln | Ala | Pro | Lys | Ala | Asp | Asn |
| Lys | Phe | Asn | Lys | Glu | Gln | Gln | Asn | Ala | Phe | Tyr | Glu | Ile | Leu |
| His | Leu | Pro | Asn | Leu | Asn | Glu | Glu | Gln | Arg | Asn | Gly | Phe | Ile |
| Gln | Ser | Leu | Lys | Asp | Asp | Pro | Ser | Gln | Ser | Ala | Asn | Leu | Leu |
| Ala | Glu | Ala | Lys | Lys | Leu | Asn | Asp | Ala | Gln | Ala | Pro | Lys | Ala |
| Asp | Asn | Lys | Phe | Asn | Lys | Glu | Gln | Gln | Asn | Ala | Phe | Tyr | Glu |
| Ile | Leu | His | Leu | Pro | Asn | Leu | Thr | Glu | Glu | Gln | Arg | Asn | Gly |
| Phe | Ile | Gln | Ser | Leu | Lys | Asp | Asp | Pro | Ser | Val | Ser | Lys | Glu |
| Ile | Leu | Ala | Glu | Ala | Lys | Lys | Leu | Asn | Asp | Ala | Gln | Ala | Pro |
| Lys | Glu | Glu | Asp | Asn | Asn | Lys | Pro | Gly | Lys | Glu | Asp | Gly | Asn |
| Lys | Pro | Gly | Lys | Glu | Asp | Gly | Asn | Lys | Pro | Gly | Lys | Glu | Asp |
| Asn | Lys | Asn | Leu | Gly | Lys | Glu | Asp | Gly | Asn | Lys | Pro | Gly | Lys |
| Glu | Asp | Asn | Lys | Lys | Pro | Gly | Lys | Glu | Asp | Gly | Asn | Lys | Pro |
| Gly | Lys | Glu | Asp | Gly | Asn | Lys | Pro | Gly | Lys | Glu | Asp | Gly | Asn |
| Lys | Pro | Gly | Lys | Glu | Asp | Gly | Asn | Lys | Pro | Gly | Lys | Glu | Asp |
| Gly | Asn | Lys | Pro | Gly | Lys | Glu | Asp | Gly | Asn | Gly | Val | Ile | Asp |
| Asp | Lys | Leu | Ser | Asn | Met | Arg | Ile | Leu | Glu | Asp | Glu | Arg | Ala |
| Ser. | | | | | | | | | | | | | |

7. An immobilized immunoglobulin-binding protein material comprising an immobilization support material covalently joined through a linker to an immunoglobulin-binding protein wherein said linker comprises arginine, and wherein said immunoglobulin-binding protein is selected from the group consisting of protein A, any of domains A, B, C, D, and E of protein A, and any combination of domains A, B, C, D, and E of protein A, and said immunoglobulin-binding protein is directly covalently joined to a terminal arginine of said linker.

8. The immobilized immunoglobulin-binding protein material, according to claim 7, wherein said immunoglobulin-binding protein is produced by recombinant means.

9. The immobilized immunoglobulin-binding protein material, according to claim 7, wherein said immunoglobulin-binding protein is joined to said linker through an amide bond.

10. The immobilized immunoglobulin-binding protein material, according to claim 7, wherein said immobilization support material is crosslinked 4% agarose.

11. The immobilized immunoglobulin-binding protein material, according to claim 7, wherein said linker is N-(2-hydroxypropyl)arginine.

12. The immobilized immunoglobulin-binding protein material, according to claim 7, wherein said immunoglobulin is human or mouse IgG1.

13. Immobilized recombinant protein A characterized as crosslinked 4% agarose joined covalently through an N-(2-hydroxypropyl)arginine linker, via an amide bond, to recombinant protein A comprising the following amino acid sequence:

| Met | Leu | Arg | Pro | Val | Glu | Thr | Pro | Thr | Arg | Glu | Ile | Lys | Lys |
|-----|-----|-----|-----|-----|-----|-----|-----|-----|-----|-----|-----|-----|-----|
| Leu | Asp | Gly | Leu | Ala | Gln | His | Asp | Glu | Ala | Gln | Gln | Asn | Ala |
| Phe | Tyr | Gln | Val | Leu | Asn | Met | Pro | Asn | Leu | Asn | Ala | Asp | Gln |
| Arg | Asn | Gly | Phe | Ile | Gln | Ser | Leu | Lys | Asp | Asp | Pro | Ser | Gln |
| Ser | Ala | Asn | Val | Leu | Gly | Glu | Ala | Gln | Lys | Leu | Asn | Asp | Ser |
| Gln | Ala | Pro | Lys | Ala | Asp | Ala | Gln | Gln | Asn | Lys | Phe | Asn | Lys |
| Asp | Gln | Gln | Ser | Ala | Phe | Tyr | Glu | Ile | Leu | Asn | Met | Pro | Asn |
| Leu | Asn | Glu | Glu | Gln | Arg | Asn | Gly | Phe | Ile | Gln | Ser | Leu | Lys |
| Asp | Asp | Pro | Ser | Gln | Ser | Thr | Asn | Val | Leu | Gly | Glu | Ala | Lys |
| Lys | Leu | Asn | Glu | Ser | Gln | Ala | Pro | Lys | Ala | Asp | Asn | Asn | Phe |
| Asn | Lys | Glu | Gln | Gln | Asn | Ala | Phe | Tyr | Glu | Ile | Leu | Asn | Met |
| Pro | Asn | Leu | Asn | Glu | Glu | Gln | Arg | Asn | Gly | Phe | Ile | Gln | Ser |
| Leu | Lys | Asp | Asp | Pro | Ser | Gln | Ser | Ala | Asn | Leu | Leu | Ala | Glu |
| Ala | Lys | Lys | Leu | Asn | Glu | Ser | Gln | Ala | Pro | Lys | Ala | Asp | Asn |
| Lys | Phe | Asn | Lys | Glu | Gln | Gln | Asn | Ala | Phe | Tyr | Glu | Ile | Leu |
| His | Leu | Pro | Asn | Leu | Asn | Glu | Glu | Gln | Arg | Asn | Gly | Phe | Ile |
| Gln | Ser | Leu | Lys | Asp | Asp | Pro | Ser | Gln | Ser | Ala | Asn | Leu | Leu |

-continued

| Ala | Glu | Ala | Lys | Lys | Leu | Asn | Asp | Ala | Gln | Ala | Pro | Lys | Ala |
|---|---|---|---|---|---|---|---|---|---|---|---|---|---|
| Asp | Asn | Lys | Phe | Asn | Lys | Glu | Gln | Gln | Asn | Ala | Phe | Tyr | Glu |
| Ile | Leu | His | Leu | Pro | Asn | Leu | Thr | Glu | Glu | Gln | Arg | Asn | Gly |
| Phe | Ile | Gln | Ser | Leu | Lys | Asp | Asp | Pro | Ser | Val | Ser | Lys | Glu |
| Ile | Leu | Ala | Glu | Ala | Lys | Lys | Leu | Asn | Asp | Ala | Gln | Ala | Pro |
| Lys | Glu | Glu | Asp | Asn | Asn | Lys | Pro | Gly | Lys | Glu | Asp | Gly | Asn |
| Lys | Pro | Gly | Lys | Glu | Asp | Gly | Asn | Lys | Pro | Gly | Lys | Gly | Asp |
| Asn | Lys | Asn | Leu | Gly | Lys | Glu | Asp | Gly | Asn | Lys | Pro | Gly | Lys |
| Glu | Asp | Asn | Lys | Lys | Pro | Gly | Lys | Glu | Asp | Gly | Asn | Lys | Pro |
| Gly | Lys | Glu | Asp | Gly | Asn | Lys | Pro | Gly | Lys | Glu | Asp | Gly | Asn |
| Lys | Pro | Gly | Lys | Glu | Asp | Gly | Asn | Lys | Pro | Gly | Lys | Glu | Asp |
| Gly | Asn | Lys | Pro | Gly | Lys | Glu | Asp | Gly | Asn | Gly | Val | Ile | Asp |
| Asp | Lys | Leu | Ser | Asn | Met | Arg | Ile | Leu | Glu | Asp | Glu | Arg | Ala |
| Ser. | | | | | | | | | | | | | |

14. In a process for binding an immunoglobulin, wherein said process comprises contacting a preparation containing an immunoglobulin with an immobilized immunoglobulin-binding material comprising an immobilization support material covalently joined through a linker to an immunoglobulin-binding protein, wherein said immunoglobulin-binding protein is selected from the group consisting of protein A, any of domains A, B, C, D, and E of protein A, and any combination of domains A, B, C, D, and E of protein A; an improvement whereby said linker comprises arginine, and said immunoglobulin-binding protein is directly covalently joined to a terminal arginine of said linker.

15. The process, according to claim 14, wherein said immunoglobulin is human or mouse IgG.

16. The process, according to claim 14, wherein said immunoglobulin-binding protein is joined to said linker through an amide bond.

17. The process, according to claim 14, wherein said immobilization support material is crosslinked 4% agarose.

18. The process, according to claim 14, wherein said linker is N-(2-hydroxypropyl)arginine.

19. In a process for binding human or mouse IgG1 which comprises contacting a preparation containing human or mouse IgG1 with an immobilized immunoglobulin-binding protein comprising an immobilization support material covalently joined, through the use of a linker, to said immunoglobulin-binding protein, and wherein said immunoglobulin-binding protein is selected from the group consisting of protein A, any of domains A, B, C, D, and E of protein A, and any combination of domains A, B, C, D, and E of protein A; an improvement wherein said linker comprises arginine, an improvement whereby said linker comprises arginine, and said immunoglobulin-binding protein is directly covalently joined to a terminal arginine of said linker.

20. The process, according to claim 19, wherein said immunmoglobulin-binding protein is recombinant protein A comprising the following amino acid sequence:

| Met | Leu | Arg | Pro | Val | Glu | Thr | Pro | Thr | Arg | Glu | Ile | Lys | Lys |
|---|---|---|---|---|---|---|---|---|---|---|---|---|---|
| Leu | Asp | Gly | Leu | Ala | Gln | His | Asp | Glu | Ala | Gln | Gln | Asn | Ala |
| Phe | Tyr | Gln | Val | Leu | Asn | Met | Pro | Asn | Leu | Asn | Ala | Asp | Gln |
| Arg | Asn | Gly | Phe | Ile | Gln | Ser | Leu | Lys | Asp | Asp | Pro | Ser | Gln |
| Ser | Ala | Asn | Val | Leu | Gly | Glu | Ala | Gln | Lys | Leu | Asn | Asp | Ser |
| Gln | Ala | Pro | Lys | Ala | Asp | Ala | Gln | Gln | Asn | Lys | Phe | Asn | Lys |
| Asp | Gln | Gln | Ser | Ala | Phe | Tyr | Glu | Ile | Leu | Asn | Met | Pro | Asn |
| Leu | Asn | Glu | Glu | Gln | Arg | Asn | Gly | Phe | Ile | Gln | Ser | Leu | Lys |
| Asp | Asp | Pro | Ser | Gln | Ser | Thr | Asn | Val | Leu | Gly | Glu | Ala | Lys |
| Lys | Leu | Asn | Glu | Ser | Gln | Ala | Pro | Lys | Ala | Asp | Asn | Asn | Phe |
| Asn | Lys | Glu | Gln | Gln | Asn | Ala | Phe | Tyr | Glu | Ile | Leu | Asn | Met |
| Pro | Asn | Leu | Asn | Glu | Glu | Gln | Arg | Asn | Gly | Phe | Ile | Gln | Ser |
| Leu | Lys | Asp | Asp | Pro | Ser | Gln | Ser | Ala | Asn | Leu | Leu | Ala | Glu |
| Ala | Lys | Lys | Leu | Asn | Glu | Ser | Gln | Ala | Pro | Lys | Ala | Asp | Asn |
| Lys | Phe | Asn | Lys | Glu | Gln | Gln | Asn | Ala | Phe | Tyr | Glu | Ile | Leu |
| His | Leu | Pro | Asn | Leu | Asn | Glu | Glu | Gln | Arg | Asn | Gly | Phe | Ile |
| Gln | Ser | Leu | Lys | Asp | Asp | Pro | Ser | Gln | Ser | Ala | Asn | Leu | Leu |
| Ala | Glu | Ala | Lys | Lys | Leu | Asn | Asp | Ala | Gln | Ala | Pro | Lys | Ala |
| Asp | Asn | Lys | Phe | Asn | Lys | Glu | Gln | Gln | Asn | Ala | Phe | Tyr | Glu |
| Ile | Leu | His | Leu | Pro | Asn | Leu | Thr | Glu | Glu | Gln | ArG | Asn | Gly |
| Phe | Ile | Gln | Ser | Leu | Lys | Asp | ASp | Pro | Ser | Val | Ser | Lys | Glu |
| Ile | Leu | Ala | Glu | Ala | Lys | Lys | Leu | Asn | Asp | Ala | Gln | Ala | Pro |
| Lys | Glu | Glu | Asp | Asn | Asn | Lys | Pro | Gly | Lys | Glu | Asp | Gly | Asn |
| Lys | Pro | Gly | Lys | Glu | Asp | Gly | Asn | Lys | Pro | Gly | Lys | Glu | Asp |
| Asn | Lys | Asn | Leu | Gly | Lys | Glu | Asp | Gly | Asn | Lys | Pro | Gly | Lys |
| Glu | Asp | Asn | Lys | Lys | Pro | Gly | Lys | Glu | Asp | Gly | Asn | Lys | Pro |
| Gly | Lys | Glu | Asp | Gly | Asn | Lys | Pro | Gly | Lys | Glu | Asp | Gly | Asn |
| Lys | Pro | Gly | Lys | Glu | Asp | Gly | Asn | Lys | Pro | Gly | Lys | Glu | Asp |
| Gly | Asn | Lys | Pro | Gly | Lys | Glu | Asp | Gly | Asn | Gly | Val | Ile | Asp |
| Asp | Lys | Leu | Ser | Asn | Met | Arg | Ile | Leu | Glu | Asp | Glu | Arg | Ala |
| Ser. | | | | | | | | | | | | | |

21. The process, according to claim 19, wherein said immobilized protein A material is characterized as crosslinked 4% agarose joined covalently through an N-(2-hyrdoxypropyl)arginine linker, via an amide bond, to recombinant protein A comprising the following amino acid sequence:

| Met | Leu | Arg | Pro | Val | Glu | Thr | Pro | Thr | Arg | Glu | Ile | Lys | Lys |

-continued

| | | | | | | | | | | | | | |
|---|---|---|---|---|---|---|---|---|---|---|---|---|---|
| Leu | Asp | Gly | Leu | Ala | Gln | His | Asp | Glu | Ala | Gln | Gln | Asn | Ala |
| Phe | Tyr | Gln | Val | Leu | Asn | Met | Pro | Asn | Leu | Asn | Ala | Asp | Gln |
| Arg | Asn | Gly | Phe | Ile | Gln | Ser | Leu | Lys | Asp | Asp | Pro | Ser | Gln |
| Ser | Ala | Asn | Val | Leu | Gly | Glu | Ala | Gln | Lys | Leu | Asn | Asp | Ser |
| Gln | Ala | Pro | Lys | Ala | Asp | Ala | Gln | Gln | Asn | Lys | Phe | Asn | Lys |
| Asp | Gln | Gln | Ser | Ala | Phe | Tyr | Glu | Ile | Leu | Asn | Met | Pro | Asn |
| Leu | Asn | Glu | Glu | Gln | Arg | Asn | Gly | Phe | Ile | Gln | Ser | Leu | Lys |
| Asp | Asp | Pro | Ser | Gln | Ser | Thr | Asn | Val | Leu | Gly | Glu | Ala | Lys |
| Lys | Leu | Asn | Glu | Ser | Gln | Ala | Pro | Lys | Ala | Asp | Asn | Asn | Phe |
| Asn | Lys | Glu | Gln | Gln | Asn | Ala | Phe | Tyr | Glu | Ile | Leu | Asn | Met |
| Pro | Asn | Leu | Asn | Glu | Glu | Gln | Arg | Asn | Gly | Phe | Ile | Gln | Ser |
| Leu | Lys | Asp | Asp | Pro | Ser | Gln | Ser | Ala | Asn | Leu | Leu | Ala | Glu |
| Ala | Lys | Lys | Leu | Asn | Glu | Ser | Gln | Ala | Pro | Lys | Ala | Asp | Asn |
| Lys | Phe | Asn | Lys | Glu | Gln | Gln | Asn | Ala | Phe | Tyr | Glu | Ile | Leu |
| His | Leu | Pro | Asn | Leu | Asn | Glu | Glu | Gln | Arg | Asn | Gly | Phe | Ile |
| Gln | Ser | Leu | Lys | Asp | Asp | Pro | Ser | Gln | Ser | Ala | Asn | Leu | Leu |
| Ala | Glu | Ala | Lys | Lys | Leu | Asn | Asp | Ala | Gln | Ala | Pro | Lys | Ala |
| Asp | Asn | Lys | Phe | Asn | Lys | Glu | Gln | Gln | Asn | Ala | Phe | Tyr | Glu |
| Ile | Leu | His | Leu | Pro | Asn | leu | Thr | Glu | Glu | Gln | Arg | Asn | Gly |
| Phe | Ile | Gln | Ser | Leu | Lys | Asp | Asp | Pro | Ser | Val | Ser | Lys | Glu |
| Ile | Leu | Ala | Glu | Ala | Lys | Lys | Leu | Asn | Asp | Ala | Gln | Ala | Pro |
| Lys | Glu | Glu | Asp | Asn | Asn | Lys | Pro | Gly | Lys | Glu | Asp | Gly | Asn |
| Lys | Pro | Gly | Lys | Glu | Asp | Gly | Asn | Lys | Pro | Gly | Lys | Glu | Asp |
| Asn | Lys | Asn | Leu | Gly | Lys | Glu | Asp | Gly | Asn | Lys | Pro | Gly | Lys |
| Glu | Asp | Asn | Lys | Lys | Pro | Gly | Lys | Glu | Asp | Gly | Asn | Lys | Pro |
| Gly | Lys | Glu | Asp | Gly | Asn | Lys | Pro | Gly | Lys | Glu | Asp | Gly | Asn |
| Lys | Pro | Gly | Lys | Glu | Asp | Gly | Asn | Lys | Pro | Gly | Lys | Glu | Asp |
| Gly | Asn | Lys | Pro | Gly | Lys | Glu | Asp | Gly | Asn | Gly | Val | Ile | Asp |
| Asp | Lys | Leu | Ser | Asn | Met | Arg | Ile | Leu | Glu | Asp | Glu | Arg | Ala |
| Ser. | | | | | | | | | | | | | |

22. The process, according to claim 19, wherein said immunoglobulin-binding protein is joined to said linker through an amide bond.

23. The process, according to claim 19, wherein said immobilization support material is crosslinked 4% agarose.

24. The process, according to claim 19, wherein said linker is N-(2-hydroxypropyl)arginine.

25. In a process for purifying a monoclonal antibody preparation, wherein said process comprises contacting said preparation with an immobilized immunoglobulin-binding material comprising an immobilization support material covalently joined through a linker to an immunoglobulin-binding protein, and wherein said immunoglobulin-binding protein is selected from the group consisting of protein A, any of domains A, B, C, D, and E of protein A, and any combination of domains A, B, C, D, and E of protein A; an improvement wherein said linker comprises arginine, and said immunoglobulin-binding protein is directly covalently joined to a terminal arginine of said linker.

26. The process, according to claim 25, wherein said monoclonal antibody preparation is an immunoglobulin of the IgG class.

27. The process, according to claim 26, wherein said IgG immunoglobulin is IgG1.

28. The process, according to claim 27, wherein said IgG1 is from a human or murine source.

29. The process, according to claim 25, wherein said immunoglobulin-binding protein is joined to the linker through an amide bond.

30. The process, according to claim 25, wherein said immobilization support material is crosslinked 4% agarose.

31. The process, according to claim 25, wherein said linker is N-(2-hydroxypropyl)arginine.

* * * * *

UNITED STATES PATENT AND TRADEMARK OFFICE
CERTIFICATE OF CORRECTION

| | | |
|---|---|---|
| PATENT NO. | : | 5,089,605 |
| DATED | : | February 18, 1992 |
| INVENTOR(S) | : | Altbert T. Profy, Margaret A. Belew, Walter C. Herlihy |

It is certified that error appears in the above-identified patent and that said Letters Patent is hereby corrected as shown below:

Column 3:   Line 25: "Ddetailed" should read --Detailed--.
Column 5:   Line 20: "well weight" should read --cell weight--; line 47: "8.3 and" should read --8.3 with--.
Column 8:   Line 61: "aid" should read --said--; line 64: "or protein A" should read --of protein A--.
Column 11:  Line 8: "Lys Pro Gly Lys Glu Asp Gly Asn Lys Pro Gly Lys Gly Asp" should read --Lys Pro Gly Lys Glu Asp Gly Asn Lys Pro Gly Lys Glu Asp--.
Column 12:  Lines 25-26: Delete duplication of lines reading "an improvement whereby said linker comprises arginine".

Signed and Sealed this

Fifteenth Day of June, 1993

Attest:

MICHAEL K. KIRK

Attesting Officer

Acting Commissioner of Patents and Trademarks